United States Patent
Smotritckii et al.

(10) Patent No.: US 10,597,629 B2
(45) Date of Patent: Mar. 24, 2020

(54) METHOD AND SYSTEM FOR PREPARATION OF SUBSTRATE FOR USE IN ANAEROBIC DIGESTION OF ORGANIC WASTE

(71) Applicant: "BIOENERGY" LIMITED LIABILITY COMPANY, Ekaterinburg (RU)

(72) Inventors: Aleksandr Andreevich Smotritckii, Ekaterinburg (RU); Andrey Vladimirovich Smotritskiy, Ekaterinburg (RU); Tatiana Andreevna Smotritskaya, Ekaterinburg (RU)

(73) Assignee: "BIOENERGY" LIMITED LIABILITY COMPANY, Ekaterinburg (RU)

( * ) Notice: Subject to any disclaimer, the term of this patent is extended or adjusted under 35 U.S.C. 154(b) by 288 days.

(21) Appl. No.: 15/057,924

(22) Filed: Mar. 1, 2016

(65) Prior Publication Data

US 2016/0177253 A1 Jun. 23, 2016

Related U.S. Application Data

(63) Continuation of application No. PCT/RU2014/000103, filed on Feb. 19, 2014.

(30) Foreign Application Priority Data

Sep. 2, 2013 (RU) ................................. 2013140555

(51) Int. Cl.
*C12N 1/00* (2006.01)
*C12M 1/00* (2006.01)
(Continued)

(52) U.S. Cl.
CPC ............. *C12M 45/20* (2013.01); *A61L 2/025* (2013.01); *A61L 2/04* (2013.01); *C05F 3/00* (2013.01);
(Continued)

(58) Field of Classification Search
None
See application file for complete search history.

(56) References Cited

U.S. PATENT DOCUMENTS 3,591,946 A * 7/1971 Loe .................... B01D 19/0068
96/175
3,904,392 A * 9/1975 VanIngen ........... B01D 19/0078
159/900

(Continued)

FOREIGN PATENT DOCUMENTS

EA 201070986 A1 4/2011
RU 2033254 C1 4/1995
(Continued)

OTHER PUBLICATIONS

Wikipedia printout, https://en.wikipedia.org/wiki/Radiator, downloaded on Oct. 6, 2016.*
(Continued)

*Primary Examiner* — Allison M Fox
*Assistant Examiner* — Qing Xu
(74) *Attorney, Agent, or Firm* — BCF LLP

(57) ABSTRACT

There is disclosed a method for preparation of substrate for use in anaerobic digestion of organic waste. The method can be executed in a substrate pretreatment system, the method comprising: loading of a substrate into the substrate pretreatment system, mixing the substrate with liquid; heating the substrate and liquid to a pre-determined processing temperature; exposing the mixture to radiation; transferring the processed substrate to a bioreactor, during the heating,
(Continued)

the method further comprises: degassing the mixture using vacuum extraction; and circulating the mixture past an ultrasonic hydrodynamic radiator.

5 Claims, 1 Drawing Sheet

(51) Int. Cl.
    *C12M 1/107*     (2006.01)
    *C05F 3/00*     (2006.01)
    *C05F 17/00*     (2020.01)
    *C12M 1/26*     (2006.01)
    *C12N 1/04*     (2006.01)
    *A61L 2/025*     (2006.01)
    *A61L 2/04*     (2006.01)
    *C12M 1/33*     (2006.01)

(52) U.S. Cl.
    CPC ......... *C05F 17/0027* (2013.01); *C12M 21/04* (2013.01); *C12M 23/02* (2013.01); *C12M 29/00* (2013.01); *C12M 29/20* (2013.01); *C12M 33/04* (2013.01); *C12M 33/07* (2013.01); *C12M 33/12* (2013.01); *C12M 45/02* (2013.01); *C12N 1/00* (2013.01); *C12N 1/04* (2013.01); *Y02P 20/145* (2015.11); *Y02W 30/43* (2015.05); *Y02W 30/47* (2015.05)

(56) References Cited

U.S. PATENT DOCUMENTS

| | | | | |
|---|---|---|---|---|
| 4,268,280 | A * | 5/1981 | Fujii | B01D 19/001 261/DIG. 10 |
| 4,944,886 | A * | 7/1990 | Masri | B01D 21/283 210/748.03 |
| 5,186,389 | A * | 2/1993 | Shibano | B08B 3/12 239/102.2 |
| 5,782,950 | A * | 7/1998 | Kanitz | C05F 3/00 71/10 |
| 5,810,037 | A * | 9/1998 | Sasaki | B08B 3/12 134/111 |
| 2002/0079266 | A1 * | 6/2002 | Ainsworth | C02F 3/28 210/603 |
| 2003/0173291 | A1 | 9/2003 | Schimel | |
| 2009/0053770 | A1 * | 2/2009 | Hennessey | C12P 7/10 435/72 |
| 2010/0108567 | A1 * | 5/2010 | Medoff | C10G 3/00 208/49 |

FOREIGN PATENT DOCUMENTS

| | | |
|---|---|---|
| RU | 2084515 C1 | 7/1997 |
| RU | 2102468 C1 | 1/1998 |
| RU | 2135437 C1 | 8/1999 |
| RU | 25845 U1 | 10/2002 |
| RU | 2207328 C2 | 6/2003 |
| RU | 2258686 C1 | 8/2005 |
| RU | 2258686 C1 * | 8/2005 |
| RU | 2315721 C1 | 1/2008 |
| RU | 2370457 C1 | 10/2009 |
| RU | 88665 U1 | 11/2009 |
| RU | 88670 U1 | 11/2009 |
| RU | 2404240 C2 | 8/2010 |
| RU | 2399184 C1 | 9/2010 |
| RU | 104286 U1 | 5/2011 |
| RU | 110588 U1 | 11/2011 |
| RU | 125995 U1 | 3/2013 |
| WO | 8808826 A1 | 11/1988 |
| WO | 0035579 A1 | 6/2000 |
| WO | 2005001976 A1 | 1/2005 |

OTHER PUBLICATIONS

Zhang et al., Bioresource Technology, 102:5048-5059, 2011.*
Gallert et al., Appl. Microbiol. Biotechnol. 48: 405-410, 1997.*
International Search Report with regard to PCT/RU2014/000103 completed on May 14, 2014.
Ariunbaatar, Javkhlan et al., "Pretreatment methods to enhance anaerobic digestion of organic solid waste", Applied Energy, Jun. 2014, vol. 123, pp. 143-156.
Montgomery, Lucie F. R. et al., "Retreatment of feedstock for enhanced biogas production", IEA Bioenergy, 2014, pp. 1-24.
English Absract (translation) of EA201070986A1 retrieved on Espacenet on Mar. 1, 2016.
English Description and Claims (translation) of RU25845U1 retrieved on Espacenet on Mar. 1, 2016.
English Description and Claims (translation) of RU88665U1 retrieved on Espacenet on Mar. 1, 2016.
English Description and Claims (translation) of RU88670U1 retrieved on Espacenet on Mar. 1, 2016.
English Description and Claims (translation) of RU104286U1 retrieved on Espacenet on Mar. 1, 2016.
English Description and Claims (translation) of RU110588U1 retrieved on Espacenet on Mar. 1, 2016.
English Claims (translation) of RU125995U1 (Machine translation retrieved on https://translate.google.ru on Feb. 29, 2016).

* cited by examiner

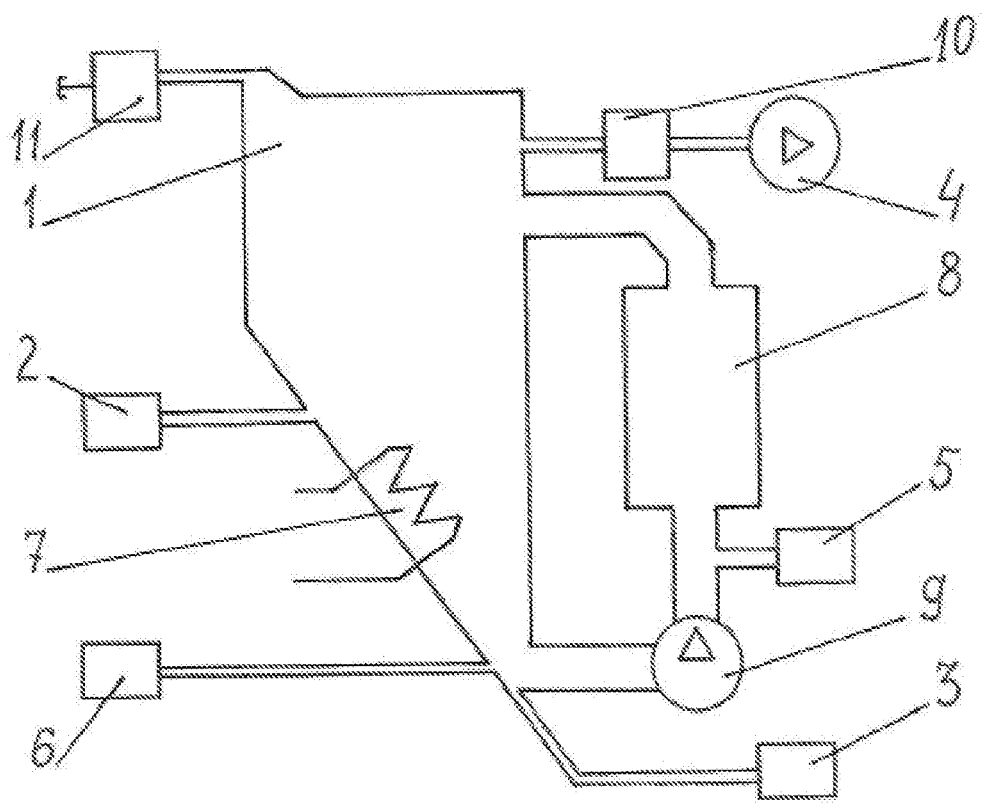

METHOD AND SYSTEM FOR PREPARATION OF SUBSTRATE FOR USE IN ANAEROBIC DIGESTION OF ORGANIC WASTE

CROSS-REFERENCE

The present application claims convention priority to Russian Utility Patent Application No. 2013140555, filed on Sep. 2, 2013, entitled "СПОСОБ ПОДГОТОВКИ СЫРЬЯ ДЛЯ АНАЭРОБНОЙ ПЕРЕРАБОТКИ ОРГАНИЧЕСКИХ ОТХОДОВ И УСТАНОВКА ДЛЯ ЕГО ОСУЩЕСТВЛЕНИЯ". This application is incorporated by reference herein in its entirety. The present application is a continuation of International Patent Application no. PCT/RU2014/000103, filed on Feb. 19, 2014, entitled "METHOD OF PREPARING RAW MATERIAL FOR ANAEROBIC DIGESTION OF ORGANIC WASTE AND INSTALLATION FOR IMPLEMENTING SAME". This application is incorporated by reference herein in its entirety.

FIELD OF THE TECHNOLOGY

This invention relates to agriculture and bioenergetics and more specifically to a method and system for preparation of substrate for use in anaerobic digestion of organic waste.

BACKGROUND

There are several known methods of organic waste processing, as well several known systems that include bioreactors, for example those disclosed in: U.S. Pat. No. 6,663,777 A1, 18 Sep. 2003. FR 2614888, 1988. RU 2084515 C1, 20 Jul. 1997. RU 2102468 C1, 20 Jan. 1998. RU 2258686, 20 Aug. 2004. RU 2315721 C1, 27 Jan. 2006. RU 2370457 C1, 20 Oct. 2009. RU 2399184 C1, 20 Sep. 2010. RU 2404240 C2, 20 Nov. 2010. RU 88665 U1, 20 Nov. 2009. RU 110588 U1, 27 Nov. 2011. RU 125995 U1, 20 Mar. 2013.

Known designs and methods for biological waste processing include creation of conditions for microbiological digestion of the substrate (i.e. waste to be processed) using methane-producing anaerobic bacteria in a single or multiple stages. Known approaches further include pretreatment of the substrate, the pretreatment techniques ranging from a simple mixing to fine milling before feeding into the bioreactor.

Traditionally, when preparing the substrate it is initially ground up, then mixed with a fluid and/or additives; then the mix is ground in preparation for feeding into the bioreactor. Mechanical milling and mixing devices are traditionally used in the process of substrate pretreatment for organic waste digestion with further addition of liquid (if necessary) and/or other components with or without heating.

Quality parameters of the raw biomass include (but are not limited to): temperature, the level of exposure to the microorganisms and the like. The biomass in its original state almost always consists of cell groups separated by various membranes and protective layers, so decomposition goes slowly and some cell groups remain un-decomposed after digestion There is a known method of substrate pretreatment that includes milling and mixing of the raw biomass using mechanical blades in a chamber connected, via perforated plate, to a fermentation chamber of the bioreactor (RU 2084515, 20 Jul. 1997).

In accordance with the RU patent 2370457, 20 Oct. 2009, in order to accelerate the fermentation process when preparing the substrate, the substrate is milled and mixed with additional liquid collected from the wet organic fertilizer drained from the anaerobic bioreactor.

There are known methods of organic waste treatment that include milling and homogenization of the organic waste using electrohydraulic charges as the organic waste travels along the length of the apparatus (RU 2135437, 27 Aug. 1999). There are also known methods where organic fertilizer is produced by means of dispersing of the organic portion of the substrate using hydro-percussive impact on the mixture in a closed loop circulation (RU 2258686, 20 Aug. 2005) or by means of ultrasonic vibration during the aerobic treatment with further magnetic treatment during the anaerobic digestion (RU 2207328, 27 Jun. 2003).

There are further known methods of substrate pretreatment where the mixture is mechanically milled or dispersed in order to break down all oversized particles, to achieve a more homogenous mixture for the bioreactor. It is believed, however, that these methods do not achieve an acceptable quality of mixture for intensive microbiological digestion.

Anaerobic digestion of less than optimally prepared biomass even under appropriate conditions takes significantly more time (as much as 2-3 times more), with biogas output being 50-200% less than in the case of a similar amount of optimally prepared biomass.

There are also known substrate pretreatment without milling (utility model RU 88665, 20 Nov. 2009). The prior art approaches attempted to improve on these systems by providing a substrate pretreatment section of a process line under the utility model patent RU 125995, 20 Mar. 2013 containing a storage hopper and a grinder that accepts large grain-sized substrate, transfer of the ground substrate to the hopper output and loading of the ground substrate from the feeding hopper to the loading-mixing conveyor. This pretreatment of the substrate requires a lot of equipment and also does not provide an optimal quality of mixture.

Mechanical rotary shredders are widely used as grinding and mixing tools for the raw biomass, for instance bladed units comprising a driveshaft installed in the chambers separated by a perforated partition feeding into the acid digestion chamber of the reactor (RU 2084515, 20 Jul. 1997).

In order to increase digestion process efficiency in the pretreatment system under the patent RU 2370457, 20 Oct. 2009 there are additional input feeds for liquid supply to the grinding chamber. This liquid is obtained from the wet organic fertilizer drained from the anaerobic bioreactor.

There is also a known installation for organic waste processing into fertilizers where the mixing, milling and homogenization occur in an electrohydraulic chamber with a row of paired electrodes placed inside (RU 2135437, 27 Aug. 1999). There is also a known biogas unit as disclosed in the patent RU 2102468, 20 Jan. 1998, where the pretreatment is realized with the use of a destructor located between the waste collector and the bioreactor. There are also known installations for organic fertilizer production, as disclosed in the patents RU 2258686, 20 Aug. 2005 and RU 2207328, 27 Jun. 2003, in RU 2258686. The first reference contemplates a rotary hydro-percussion device for breaking down the mixture while it circulates in a closed loop, while the second references relies on an ultrasonic vibration generator for the ultrasonic breaking down the mixture for aerobic treatment.

There is also a known biological waste digestion unit as disclosed in European Patent 1636869, 22 May 2008. There is disclosed a substrate pretreatment system for substrate pretreatment for anaerobic digestion of organic waste. This pretreatment system includes a substrate and water mixing device and a number of ultrasonic radiators for ultrasonic processing located around the bioreactor's substrate access channel. The ultrasonic radiator device corresponds to that described in WO 0335579, 22 Jun. 2000, consisting of a chamber and many ultrasonic transducers attached to the outer wall of the chamber. Sixty modules of 50 kW piezoelectric transducers each resonating at 20 kHz are tightly packed in a grid and form five rings around the chamber, 12 modules per ring.

This method increases the rate of hydrolysis and the release of water-soluble substances from the waste, making these substances more exposed to the microorganisms. However the efficiency of this method is believed to be low as the ultrasonic emitters require much time and energy in order to achieve the desired effect. Therefore the quality of the mixture is not believed to be adequate.

Further improvement of the mixture is still possible so as to increase bioreactor efficiency—the most costly element of biogas production.

SUMMARY OF THE TECHNOLOGY

Developers of the present technology developed embodiments of the present invention based on their appreciation for a need for further development in the area for biotechnology for organic waste disposal.

Inventors have aimed to develop methods and systems that intensify the biological processes due to the increase of the biological agents' potential. Certain embodiments of the present technology include pretreatment of the substrate in order to create a nutrient-rich medium for microorganisms' growth so as to get an adequate quality mixture for the main bioreactor.

Developers of the present technology have further appreciated that known pretreatment units with mechanical grinders and destroyers that block oversized fragments from entering the bioreactor are ineffective and do not provide adequate quality mixture, thus requiring bioreactors of more complex design to ensure a more thorough anaerobic treatment of organic wastes.

Embodiments of the present invention aim to increase the efficiency of the pretreatment of the substrate so as to provide an increase in anaerobic digestion speed and intensity.

Broadly speaking, embodiments of the present invention aim to increase the quality of the mixture by means of fine dispersing, disinfection and homogenization, which result in a comparatively faster digestion and an increase in the product yield while decreasing substrate costs. It is believed that embodiments of the present invention have application in (but not limited to): area of fertilizers and biogas with the purpose of allowing for local ecological stabilization in areas where waste concentrations occur (animal and poultry manure, agricultural and agro-industrial wastes, waste food etc.).

According to a first broad aspect of the present technology, there is provided a method for preparation of substrate for use in anaerobic digestion of organic waste. The method can be implemented in a substrate pretreatment system. The method comprises: loading of a substrate into the substrate pretreatment system, mixing the substrate with liquid; heating the substrate and liquid to a pre-determined processing temperature; exposing the mixture to radiation; transferring the processed substrate to a bioreactor, during the heating, the method further comprises: degassing the mixture using vacuum extraction; and circulating the mixture past an ultrasonic hydrodynamic radiator.

In some embodiments of the method, the substrate pretreatment system comprises an airtight chamber, and wherein said circulating is executed in a closed loop within the airtight chamber.

In some embodiments of the method, the method further comprises supplying an oxygen-free gas to a radiator chamber of the ultrasonic hydrodynamic radiator.

In some embodiments of the method, the supplying an oxygen-free gas to a radiator chamber comprises supplying gas collected from the bioreactor.

In some implementations of the method, the method further comprises draining a liquid fraction from the bioreactor and using the drained liquid fraction as the liquid for mixing with the substrate.

In accordance with another broad aspect of the present technology there is provided a substrate pretreatment system for organic waste anaerobic digestion. The substrate pretreatment system is for use with a bioreactor. The substrate pretreatment system comprises: an airtight chamber; a source of organic substrate and a source of fluid coupled to the airtight chamber; a heater for heating the airtight chamber; a gas source coupled to the airtight chamber; a substrate output for supplying the substrate to the bioreactor; the airtight chamber further including a vacuum pump and an ultrasonic hydrodynamic radiator, the ultrasonic hydrodynamic radiator having a radiator chamber coupled to the airtight chamber forming a closed loop.

In some implementations of the system, the chamber of the ultrasonic hydrodynamic radiator is equipped with an oxygen-free gas supply unit.

In some implementations of the system, the oxygen-free gas supply unit is connected to the bioreactor.

In some implementations of the system, the source of fluid is coupled to a bioreactor draining system of the bioreactor.

In some embodiments of the present technology, the pretreatment process is implemented in a single airtight chamber, such that the ultrasonic hydrodynamic treatment of the mixture is performed during circulation in a closed loop within the airtight chamber. An oxygen-free gas is supplied to the chamber of the ultrasonic hydrodynamic pretreatment chamber. This oxygen-free gas can be supplied directly from the bioreactor, and the liquid drained from the bioreactor can be used as the liquid for mixing with the substrate.

Certain embodiments of the present invention provide an anaerobic digestion substrate pretreatment installation that includes: devices for adding liquid to the substrate, heating, ultrasonic treatment and substrate dispensing into the bioreactor. As opposed to the prior art pretreatment installations, embodiments of the present technology is equipped with an airtight chamber furnished with a vacuum pump, and the ultrasonic treatment device is implemented as an ultrasonic hydro-dynamic radiator with its chamber making a closed loop with the airtight chamber.

Furthermore the ultrasonic hydrodynamic radiator chamber is equipped with an oxygen-free gas supply device which can be connected to the bioreactor, and a liquid supply device for substrate mixing is connected to the bioreactor drainage system.

BRIEF DESCRIPTION OF THE DRAWINGS

Embodiments of the present technology will be described with reference to drawings, in which:

FIG. 1 depicts a schematic illustration of a substrate pretreatment installation for organic waste anaerobic processing, the substrate pretreatment installation being implemented in accordance with non-limiting embodiments of the present technology.

DETAILED DESCRIPTION OF THE EMBODIMENTS

With reference to FIG. 1, the substrate pretreatment installation includes an airtight chamber 1. The substrate pretreatment installation can be used as part of a system that includes a bioreactor (not depicted). The airtight chamber 1 is coupled to a source of organic substrate 2 and a source of fluid 3 (these are referred together, from time to time, as sources of organic substrate and fluid 2,3).

The airtight chamber 1 is further coupled to a vacuum pump 4 and a gas source 5. The gas source 5 is configured for supplying gas from the bioreactor (not depicted). The airtight chamber 1 is further coupled to a substrate output 6 for supplying the processed substrate to the bioreactor (not depicted).

The airtight chamber 1 further comprises a heater 7 and an ultrasonic hydrodynamic radiator 8. The ultrasonic hydrodynamic radiator 8 can be implemented as a laminar or a rod type. A radiator chamber (not separately numbered) of the ultrasonic hydrodynamic radiator 8 is connected to the airtight chamber 1 via a pump 9 forming a closed circulation loop therewith.

The installation of FIG. 1 is configured to implement a method of pretreatment of substrates as follows.

The airtight chamber 1 is configured to receive substrate. The substrate is received from a storage hopper (not depicted) via the source 2. The airtight chamber 1 is further configured to receive a heated liquid from the wet organic fertilizer drained from the bioreactor via the source 3. The supply of the substrate and liquid can be done under pressure.

Once the airtight chamber 1 is loaded, the temperature of the mixture is determined, then heater 7 is turned on in order to heat the mixture to a pre-determined operational temperature of a first stage of the bioreactor process. This temperature can be, as an example, 37° C.

The vacuum pump 4 is configured to implement a degassing process simultaneously with the mixture heating. The degassing process can be executed, as an example, for 15-20 minutes. Vacuuming helps to evacuate unwanted vapors and to remove the bulk of the oxygen dissolved in the substrate (as it is poisonous for the microorganisms performing in the digestion). Then vacuum pump 4 is switched off, the line is closed by a valve 10. The pump 9 is then switched on, the ultrasonic hydrodynamic radiator 8 starts and gas supply is commenced via the gas source 5 from the bioreactor.

The mixture is simultaneously heated and circulated in a closed loop past the ultrasonic hydrodynamic radiator 8. Surplus gas is evacuated via a valve 11.

As a result of the recirculation past the ultrasonic hydrodynamic radiator 8 the fluid is made turbulent by the vibrations of the mechanical resonators and the oscillations of these resonators also cause harmonic oscillations in the fluid through the form of periodic pressure impulses.

Periodic impulses simulate natural frequency oscillations by providing feedback and continuous acoustic excitation. As a result the amplitude of the oscillations increases due to resonance with oscillations of the radiator 8 mechanical resonators' oscillations.

This increased vibration causes cavitation bubbles to form, which act to break down the cell walls and provide an intensified breaking down of the mixture. Under the influence of the acoustic and ultrasonic waves excess pressure and tensile stresses appear in the fluid, hence oxidation-reduction processes start at the border of the liquid and solid phases, so a stable emulsion with high dispersion of fine particles is achieved.

Additional supply of oxygen-free gas to the cavitation zone via gas source 5 facilitates the creation of developed cavitation flow, optimizes the process and generates multiple tiny carbon dioxide bubbles. These bubbles are supplied to the bioreactor and serve as food for the methanogens, i.e. they promote increase the methane content of the biogas. Processing lasts for 10-30 minutes and finishes when the mixture is heated to the predetermined temperature. After the treatment the substrate is pumped to the bioreactor through the substrate output 6. Then the pretreatment process is repeated.

The operation of the installation of FIG. 1 can be fully automated.

Thus within the airtight chamber 1, the mixture is simultaneously heated, degassed and thoroughly treated, significantly increasing the efficiency of the process of high quality pretreatment of substrates of many kinds.

An installation equipped with the chamber of 1.5 m3 and a purge pump with capacity of 20-50 m3/hour, provides pretreatment of 50 m3 of substrate per day.

It was established experimentally that in some embodiments of the present technology, the duration of chicken manure digestion by the proposed method in the claimed substrate pretreatment installation decreases from 14 to 9 days, and the amount of received biogas increases 2.2 fold. Moreover, as a result of oxygen removal from the mixed components the reaction starts faster and carbon dioxide contents in the biogas are lowered.

Embodiments of the present technology can be implemented within a pretreatment flow line by means of serial installation of the disclosed equipment.

The invention claimed is:

1. A method for preparation of a substrate for use in anaerobic digestion of organic waste, the method being implemented in a substrate pretreatment system, the method comprising:
   a) simultaneously loading under pressure into an airtight chamber within the substrate pretreatment system i) an organic substrate, wherein the organic substrate comprises a liquid and a solid phase of the organic waste; and ii) a heated organic fluid from a bioreactor, to form a mixture;
   b) simultaneously heating and degassing the mixture, wherein the mixture is heated to and maintained at a temperature of about 37° C. to sustain growth of microorganisms;
   c) subjecting the mixture of step b) to treatment of an ultrasonic hydrodynamic device in a closed loop to create vibrations in the mixture that cause: i) periodic pressure; ii) cavitation; or iii) both i) and ii) to break down cell walls within the ultrasonic hydrodynamic device comprising a radiator which is connected to the airtight chamber to form the closed loop, and wherein the mixture is circulating within the closed loop during the treatment; and
   d) transferring the mixture of step c) to the bioreactor.

2. The method of claim 1, further comprising supplying an oxygen-free gas within the airtight chamber.

3. The method of claim 2, wherein the oxygen-free gas is supplied from the bioreactor.

4. The method of claim 1, wherein the liquid is supplied from the bioreactor.

5. The method of claim 1, wherein the degassing is performed by creating a vacuum in the substrate pretreatment system.

* * * * *